United States Patent [19]

Watanabe et al.

[11] Patent Number: 4,647,532

[45] Date of Patent: Mar. 3, 1987

[54] METHOD FOR DETERMINATION OF HYDROGEN PEROXIDE BY CHEMILUMINESCENCE ANALYSIS

[75] Inventors: Haruo Watanabe, Ayabe; Noboru Mitsuhida, Tsuruga; Makoto Andoh; Hakuji Matsumoto, both of Ohtsu, all of Japan

[73] Assignee: Toyo Boseki Kabushiki Kaisha, Osaka, Japan

[21] Appl. No.: 714,743

[22] Filed: Mar. 22, 1985

[30] Foreign Application Priority Data

Mar. 21, 1984 [JP] Japan .................................. 59-56719

[51] Int. Cl.$^4$ .................... C12Q 1/28; G01N 21/76; G01N 33/52; G01N 33/66
[52] U.S. Cl. .......................... 435/28; 436/135; 436/172
[58] Field of Search ............... 436/546, 63, 135, 166, 436/172, 803, 95, 518, 536; 423/581, 582, 586, 587, 588, 584, 590; 252/700; 435/188, 5, 7, 25, 27, 28, 29, 184

[56] References Cited

U.S. PATENT DOCUMENTS

| | | | |
|---|---|---|---|
| 3,087,794 | 4/1963 | Free et al. | 436/63 X |
| 3,564,588 | 2/1971 | Soli | 252/700 X |
| 3,597,362 | 8/1971 | Bollyky et al. | 436/135 X |
| 3,718,599 | 2/1973 | Rauhue | 252/700 |
| 3,816,326 | 6/1974 | Bollyky | 252/700 |
| 4,228,150 | 10/1980 | Robyt et al. | 435/184 X |
| 4,234,680 | 11/1980 | Hevey et al. | 435/28 X |
| 4,269,938 | 5/1981 | Frank | 252/700 X |
| 4,282,325 | 8/1981 | Rubenstein et al. | 435/188 X |
| 4,487,830 | 11/1984 | Coates et al. | 435/28 X |
| 4,491,634 | 1/1985 | Frenzel | 436/536 |

FOREIGN PATENT DOCUMENTS 0137397 10/1979 Japan .................................. 435/28
0187858 11/1983 Japan .................................. 436/166

OTHER PUBLICATIONS

*The Condensed Chemical Dictionary*—10th Ed., Revised by G. Hawley, Copyright 1981.
DeChatelet, L. R., et al., J. Immunol., 129, No. 4, 1589–1593 (10/82).
Descamps–Latscha, B., et al., Ann. Immunol., 133C, 349–364 (1982).
De Sole, P., et al., Adv. Exp. Med. Biol., 141, 591–601 (1982).
Minkenberg, I., et al., J. Immunol Methods, 71, 61–67 (1984).

*Primary Examiner*—Barry S. Richman
*Assistant Examiner*—J. Johnston

[57] ABSTRACT

A method for determination of hydrogen peroxide by chemiluminescence analysis which consists of reacting a sample containing hydrogen peroxide with an oxidizable non-fluorescent substance in the presence of an oxidizing catalyst to convert the non-fluorescent substance to a fluorescent substance, reacting the fluorescent substance with an oxalic acid di-ester and hydrogen peroxide in the presence of an inhibitor which inactivates the oxidizing catalyst, and then measuring the amount of light emission produced to determine the amount of hydrogen peroxide contained in the sample. Determination and enzyme immunoassay for a component other than hydrogen peroxide in a sample from living body and evaluation of bactericidal activity in phagocytosis of leukocytes by utilizing this method are also disclosed.

31 Claims, 6 Drawing Figures

METHOD FOR DETERMINATION OF HYDROGEN PEROXIDE BY CHEMILUMINESCENCE ANALYSIS

FIELD OF THE INVENTION

The present invention relates to a novel method for determination of hydrogen peroxide by chemiluminescence analysis. The method of the present invention can be utilized in, for example, clinical diagnostic tests including enzyme immunoassay tests to determine various components in human body fluid and the like.

BACKGROUND OF THE INVENTION

Methods for determination of hydrogen peroxide by chemiluminescence analysis are well-known in the prior art. For example, Luminol-peroxidase methods have been described by DeChatelet, L. R. et al., J. Immunol., 129, 1589–1593 (1982); Descamps-Latscha, B. et al., Ann. Immunol., 133, 349–364; and De Sole, P. et al., Adv. Exp. Med. Biol., 141, 591–601 (1982). A Lucigenin-peroxidase method has been described by Minkenberg, I. and Ferber, E., J. Immunol. Methods, 71, 61–67 (1984). However, these prior art methods have the disadvantage that their sensitivities are insufficient for determination of hydrogen peroxide unless they are performed under basic conditions. Moreover, when the above known chemiluminescence analysis methods are used for biochemical tests in the field of clinical diagnosis, they are severely affected by components in samples from a living body such as serum, urine, and the like, which result not only in reduction of light emission activity but also in low reliability of data due to variability. Although attempts have been made to overcome this problem by reducing sample amount to reduce living body component amount, this results in the disadvantage of lowering sensitivity.

In order to obtain a novel highly sensitive method for determination of hydrogen peroxide by chemiluminescence analysis without any interference from living body components, the present inventors have carried out an intensive study. As a result, it was found that the reaction of an oxalic acid di-ester with a fluorescent substance and hydrogen peroxide makes it possible to determine the amount of light emmision quantitatively without any adverse effect from body components. However, this reaction had to be performed in an organic solvent and is therefore unsuitable for use in clinical diagnostic tests because such tests are usually performed in an aqueous system. Then, the present inventors carried out a further intensive study and found that it is possible to determine hydrogen peroxide in an aqueous reaction system quantitatively with high sensitivity without any serum catalase effect by reacting hydrogen peroxide in an aqueous reaction system with an oxidizable non-fluorescent substance in the presence of an oxidizing catalyst to give a fluorescent substance, and then reacting the resulting fluorescent substance with an oxalic acid di-ester and freshly added hydrogen peroxide in an organic solvent under conditions for inhibition of the oxidizing catalyst to determine the amount of light emission. In addition, it has been also found that this reaction sequence can be utilized not only for determination of hydrogen peroxide per se contained in samples directly but also for determination of various components other than hydrogen peroxide in samples indirectly through quantitative formation of hydrogen peroxide from various reactions of the components and suitable reagents. For example, this reaction sequence can be utilized in enzyme immunoassay and other clinical diagnostic tests for determination of various components in samples from a living body. Further, it has been also found that the method of the present invention can be applied to evaluation of bactericidal activity in phagocytosis of leukocytes such as macrophages and neutrophilis because they release hydrogen peroxide and/or superoxide anion ($O_2^-$) when they exhibit bactericidal activity.

OBJECTS AND SUMMARY OF THE INVENTION

One object of the present invention is to provide a novel highly sensitive method for determination of hydrogen peroxide by chemiluminescence analysis.

Another object of the present invention is to provide a novel method for determination of various components other than hydrogen peroxide in samples from a living body including a human being.

Still another object of the present invention is to provide a novel enzyme immunoassay by chemiluminescence analysis.

Still another object of the present invention is to provide a novel method for evaluation of bactericidal activity in phagocytosis of leukocytes.

These objects as well as other objects and advantages of the present invention will become apparent to those skilled in the art from the following description and the accompanying drawings.

According to the present invention, there is provided a method for determination of hydrogen peroxide by chemiluminescence analysis which comprises reacting a sample containing hydrogen peroxide with an oxidizable non-fluorescent substance in the presence of an oxidizing catalyst to convert the non-fluorescent substance to a fluorescent substance, reacting the fluorescent substance with an oxalic acid di-ester and hydrogen peroxide under conditions for inhibition of the oxidizing catalyst, and then measuring the amount of light emission produced to determine the amount of hydrogen peroxide contained in the sample. In the method of the invention for determination of various components in samples from a living body, hydrogen peroxide is formed quantitatively by known reactions according to the amounts of the objective components to be determined and then hydrogen peroxide thus formed is determined by the above method. Likewise, in the enzyme immunoassay and the evaluation of bactericidal activity in phagocytosis of leukocytes of the present invention, hydrogen peroxide is formed quantitatively according to the amounts of the objective components or factors to be determined and then hydrogen peroxide thus formed is determined by the above method. According to these methods of the present invention, the desired results can be obtained by using minimal amounts of samples.

DETAILED DESCRIPTION OF THE INVENTION

The method of the present invention for determination of hydrogen peroxide by chemiluminescence analysis is represented by the formulas:

That is, according to the present invention, the determination of hydrogen peroxide in a sample such as a living body origin sample containing hydrogen peroxide is performed by quantitatively converting a non-fluorescent substance oxidizable by hydrogen peroxide in the sample into a fluorescent substance in the presence of an oxidizing catalyst as shown in the formula (1) (first reaction), and then, under conditions for inhibition of the oxidizing catalyst, for example, after inhibition of the catalyst with addition of an inhibitor, causing emission of liminescence from the resulting fluorescent substance in the presence of an oxalic acid di-ester and freshly added hydrogen peroxide according to the formula (2) (second reaction) and determining the amount of light emission. It is theorized that dioxetanedione formed by the reaction of the oxalic acid di-ester and hydrogen peroxide transfers energy to the fluorescent substance to cause emission of luminescence therefrom.

The samples containing hydrogen peroxide to which the method of the present invention can be applied are, for example, those containing hydrogen peroxide per se from a living body including a human being, or those containing hydrogen peroxide and/or superoxide anion derived from various components of a living body such as human body fluid, for example, blood, urine, saliva, tears and the like by known reactions. Examples of such components of a living body include uric acid, cholesterols, glucose, creatinine, polyamines, triglycerides, lactates, pyruvates, fatty acids, amylase, cholinesterase, glutamate-pyruvate transaminase and the like. The method of the present invention can also be applied to samples containing various physiologically active substances which can be determined by enzyme immunoassay, for example, peptide hormones, steriod hormones, fetal proteins (e.g., AFP, CEA, etc.), immunoglobulins, antiviral antibodies developed in various infections, autoantibodies developed in collagen disease and the like. In addition, as mentioned above, the method of the present invention can be applied to evaluation of bactericidal activity in phagocytosis of leukocytes such as macrophages and neutrophils.

Examples of the oxidizable non-fluorescent substance used in the method of the present invention include leucofluorescein (fluorescin), 2′,7′-dichlorofluoresceine-diacetate (leucodiacetyl-2,7-dichlorofluoresceine, hereinafter referred to as LDADCF) and the like. Substances such as leucorhodamin, leucoeosin, and the like which emit luminescence by oxidation of their reduced forms can also be used as the oxidizable non-fluorescent substance. Further, substances such as homovanillic acid, p-cresol, 3-(p-hydroxyphenyl)propionic acid, thryamine and the like which emit luminescence by oxidation polymerization thereof in the presence of hydrogen peroxide can be used as the oxidiazble non-fluorescent substance. The amount of the non-fluorescent substance used is preferably in the range of 0.001 to 5 mM in the reaction system.

Examples of the oxidizing catalyst used in the method of the present invention include enzymes such as peroxidase, microperoxidase, myeloperoxidase, hemin, hematine, catalase and the like and chemical oxidizing agents such as potassium ferricyanide and the like. The amount of the enzyme oxidizing catalyst used is preferably 1 to 100 units/ml of the reaction system.

The oxalic acid di-ester used in the method of the present invention includes bis(2,4,6-trichlorophenyl)oxalate (hereinafter referred to as TCPO), bis(2,4-dinitrophenyl)oxalate and the like. The amount of the oxalate is preferably in the range of 0.1 to 50 mM in the reaction system.

The inhibitor for the oxidizing catalyst used in the method of the present invention includes potassium cyanide, sodium cyanide, sodium azide, sulfides, fluorides, hydroxyphenylhydrazine, 2,3-dimercaptopropanol, and organic solvents such as ethyl acetate, acetonitrile, ethanol, acetone and the like. Particularly, by using organic solvents, the oxidizing catalyst is conveniently inhibited.

In the present invention, it is necessary to perform the first reaction in an aqueous system. In general, this reaction is performed at a temperature of about 20° to 30° C. at pH 5 to 9. After completion of the first reaction, the oxidizing catalysts should be inhibited. Where the oxidizing catalyst remains without inactivation, an excess amount of the fluorescent substance is produced by the reaction of the residual non-fluorescent substance with freshly added hydrogen peroxide in the above second reaction, which introduces a false result. Addition of $10^{-5}$ to $10^{-1}$M of a cyclodextrin such as β-cyclodextrin to the first reaction system stabilizes the non-fluorescent substance and increases emission of the fluorescent substance.

In the method of the present invention, in order to prevent oxidation of the non-fluorescent substance (leucofluorescein) in the presence of the oxidizing catalyst (peroxidase), it is preferable to add zinc sulfate hepta hydrate to the first reaction system, desirably, to produce a final concentration of zinc sulfate hepta hydrate of about 0.04 mg/ml.

The second reaction is performed in an organic solvent containing water. The organic solvent includes ethyl acetate, acetone, acetonitrile and the like. The organic solvent may be used alone or in a combination thereof. As mentioned above, this organic solvent also acts as the inhibitor of the oxidizing catalyst. In general, the second reaction is performed at a temperature of about 20° to 40° C. under basic conditions such as at pH of 8 to 12.

The amount of hydrogen peroxide added to the second reaction system is generally 0.1 to 50 mM.

The light emission activity in the second reaction system is measured according to a conventional technique. For example, the amount of peak emission is counted with a LUMIPHOTOMETER TD4000 (manufactured by LABOSCIENCE CO., LTD.). Since the light emission activity is always expressed as the amount of light emission per unit reaction time, it directly represents the reaction rate.

According to the method of the present invention, hydrogen peroxide can be quantitatively determined with high sensitivity by using chemiluminescence analysis without any interference in samples from a living body.

It has been hitherto considered that the sensitivity of the quantitative determination of hydrogen peroxide by using bis(2,4,6-trichlorophenyl)oxalate and a fluorescent substance is very low and that, usually, hydrogen peroxide can not be detected unless the amount thereof is more than $10^{-7}$ to $10^{-6}$M. However, in the method of the present invention, hydrogen peroxide can be detected even in such a small amount as $10^{-9}$M by selecting the oxidizable non-fluorescent substance.

In case of determination of various components other than hydrogen peroxide in samples from a living body by using the method of the present invention, various enzymatic oxidation reactions or reactions of $H_2O_2$ generating reagents with the components are performed separately or at the same time of the first reaction in the aqueous system to form hydrogen peroxide quantitatively. Hydrogen peroxide thus formed is determined according to the above formula (1) and (2). For example, in determination of glucose, an accompanying $H_2O_2$ generating reaction involves reaction of glucose in the presence of glucose oxidase under mild conditions so as not to damage the glucose oxidase. Moreover, reduced nicotinamide adenine dinucleotide (NADH) is readily determined by use of methylene blue as the $H_2O_2$ generating agent.

According to the present invention, such an extremely small amount of hydrogen peroxide as in the range of $10^{-9}$ to $10^{-5}$M, which is formed from a component in a sample from a living body by an accompanying reaction as mentioned above, can be determined with high sensitivity. Further, in analysis of a component in a living body, by using the method of the present invention, an actually quantitative analysis can be performed with high sensitivity without interference with the reaction in the aqueous reaction system to produce the stable fluorescent substance, and without decrease in hydrogen peroxide formed due to the action of catalase, etc. on a sample from a living body. Particularly, in the method of the present invention, the second reaction is hardly affected by interfering substances in samples from a living body and, therefore, high sensitivity in light emission activity can be attained.

In the case of applying the method of the present invention to enzyme immunoassay for determination of physiological active substances in living body, an enzyme which is capable of formation of hydrogen peroxide can be used as a labelling enzyme and hydrogen peroxide formed can be determined by the above method of the present invention to evaluate the activity of the enzyme. Further, even where hydrogen peroxide is not formed, the method of the present invention can also be applied to enzyme immunoassay using peroxidase, which can catalyze the reaction (1) in the presence of hydrogen peroxide added, as a labelling enzyme.

That is, according to the enzyme immunoassay based on chemiluminescence analysis of the present invention, a physiologically active substance in a sample from a living body can be determined by performing an immunological reaction using an enzyme being capable of formation of hydrogen peroxide as a labelling enzyme, adding a substrate for the enzyme to form hydrogen peroxide, and subjecting hydrogen peroxide thus formed to the above reactions represented by the formulas (1) and (2). Further, when peroxidase is used as a labelling enzyme, hydrogen peroxide and the oxidizable non-fluorescent substance are added after an immunological reaction to convert the non-fluorescent substance into the fluorescent substance and then the fluorescent substance is reacted with the oxalic acid di-ester added and hydrogen peroxide contained in the reaction system to emit luminescence from the fluorescent substance and the amount of light emission is determined.

By the way, the term "enzyme immunoassay" used herein means a method for determination of a physiologically active substance in a sampe from living body such as body fluid by using an antibody having selectivity for the physiologically active substance and a labelling enzyme bound antigen or using the antibody, a substrate for the enzyme and, if necessary, an insoluble carrier (solid phase) and subjecting them to an antigen-antibody reaction having high specificity. Typical enzyme immunoassay includes a competition technique and a sandwich technique and, hereinafter, the enzyme immunoassay of the present invention is further illustrated in detail according to the sandwich technique. For convenience, a physiologically active substance to be determined is represented by Ag and an antibody which is specific for binding to the physiologically active substance is represented by Ab.

Firstly, Ab is bound to a suitable known solid phase according to a known method. For example, a solid phase such as a polystyrene ball or a polystyrene tube is dipped in a solution of Ab in a suitable buffer solution at 4° C. to room temperature for several hours to overnight and washed. The Ab bound solid phase thus obtained is reacted with a sample containing an unknown amount of Ag and the excess sample is washed out. Then, an enzyme-labelled antibody prepared by labelling Ab with an enzyme which is capable of formation of hydrogen peroxide is reacted with the Ab bound solid phase to bond the enzyme-labelled antibody to the previously bonded Ag. After reaction, the excess enzyme-labelled antibody is washed out.

Examples of the enzyme being capable of formation of hydrogen peroxide include glucose oxidase, cholesterol oxidase, choline oxidase, an amino acid oxidase and the like. Although, in the present invention, the enzyme is not limited to a specific one, glucose oxidase is preferred because it is readily available at a low price and it is stable.

On the resulting solid phase thus reacted, a complex of Ab-Ag-Ab-enzyme is formed and the amount of the enzyme bound to the solid phase is proportional to that of Ag in the sample. Therefore, the amount of Ag can be determined based on the amount of the bound enzyme. In the enzyme immunoassay of the present invention, the amount of the bound enzyme is determined based on chemiluminescence analysis.

That is, a substrate of the enzyme is added to the solid phase on which the above complex has been formed. For example, when the enzyme used is glucose oxidase, the substrate is a solution of glucose in a suitable buffer solution. Then, the mixture is allowed to react at 4° to 40° C., preferably, 25° to 37° C. for at least thirty minutes to overnight, preferably, for 1 hour or more. One of the advantages of this method is that a sufficient amount of hydrogen peroxide can be accumulated in the reaction mixture by using the enzyme which is capable of formation of hydrogen peroxide in the above enzymatic reaction so that the sensitivity of the determination can be significantly improved. Hydrogen peroxide thus accumulated in the reaction mixture is determined according to the reactions of the above formulas (1) and (2). The amount of light emission is proportional to the amount of hydrogen peroxide in the formula (1) which is further proportional to the amount of the labelling enzyme, that is, the amount of Ag in the sample.

As mentioned above, the method of the present invention is also preferably applied to enzyme immunoassay using peroxidase as the labelling enzyme. In the case of the sandwich technique, Ab is labelled with peroxidase according to a known method by using a suitable solid phase. For example, peroxidase-labelled Ab bound to a solid phase is readily prepared by oxidizing a saccharide chain contained in peroxidase with periodic acid to form an aldehyde group and binding the aldehyde group to an amino group of Ab. According to the same procedure as the above sandwich technique, the resulting peroxidase-labelled Ab bound to the solid phase is reacted with a sample containing an unknown amount of Ag to obtain Ab-Ag-peroxidase-labelled Ab complex bound to the solid phase. Then, hydrogen peroxide and the oxidizable non-fluorescent substance are added to the reaction mixture to cause the reaction of the formula (1). This method is more advantageous than the above method using the enzyme which is capable of formation of hydrogen peroxide because, apart from the above method, there is no step for formation of hydrogen peroxide by an enzymatic reaction in this method. Then, after addition of peroxidase inhibitor to inactivate peroxidase, the oxalic acid di-ester is added to cause the reaction of the formula (2). Since hydrogen peroxide added to the reaction (1) also takes part in the reaction (2), there is no need to add further hydrogen peroxide in the reaction (2). The amount of light emission is measured as mentioned above to determine the amount of Ag in the sample.

It will be apparent to those skilled in the art that not only the sandwich technique using a solid phase but also other techniques such as a competition technique, the double antibody sandwich technique and the like can be employed in the enzyme immunoassay of the present invention.

Further, in case of applying the method of the present invention to evaluation of bactericidal activity in phagocytosis of leukocytes such as macrophages and neutrophils, the leukocytes are cultivated in a culture medium and phagocytosis thereof is stimulated by addition of opsonized zymosan to activate their NADPH oxidase systems and to release $O_2^-$ which exhibits bactericidal activity. Then, $O_2^-$ thus released is converted into hydrogen peroxide by action of dismutase, and hydrogen peroxide thus formed is released in the culture medium. This hydrogen peroxide is determined by the above method of the present invention according to the reactions of the formulas (1) and (2). The above formation of hydrogen peroxide and the reaction of the formula (1) are performed in an aqueous system containing a buffer at pH of 5 to 9. These reactions are not affected by leukocytes present and, even if a clouded sample is used, the emission intensity in the reaction of the formula (2) is not decreased. Therefore, by determining increase of the amount of light emission, that is, the amount of hydrogen peroxide in a sample collected at regular time intervals, the initial release rate of hydrogen peroxide can be evaluated. Further, the amount of hydrogen peroxide released can be determined as the total amount or the peak height of light emission by incubation of leukocytes with the reagents. Usually, the light emission reaction reaches the peak value within 5 seconds and, therefore, bactericidal activity in phagocytosis of leukocytes can be evaluated within a very short period of time.

The following examples further illustrate the present invention in detail but are not to be construed to limit the scope thereof.

EXAMPLE 1

A solution containing a known amount of hydrogen peroxide (0.1 ml), a solution of peroxidase (0.1 ml, 10 units/ml), a solution of zinc sulfate hepta hydrate (0.1 ml, 0.2 mg/ml) and 25 mM phosphate buffer solution containing 1 mM fluorescin (0.2 ml) were placed in a vial and reacted at 25° C. for 5 minutes. After completion of the reaction, to the reaction solution was immediately added a solution (0.5 ml) of 2 mM hydrogen peroxide, 40 mM borate buffer solution (pH 10.5) and 0.5 mM TCPO in a mixed solvent of ethyl acetate/borate buffer solution/acetonitrile (1:1:8, v/v). After 3 seconds, the light emission intensity was measured. The results are shown in FIG. 1 wherein the emission intensities (ordinate, relative values), Io, are plotted against the concentrations of hydrogen peroxide (abscissae, M).

Figure 1:
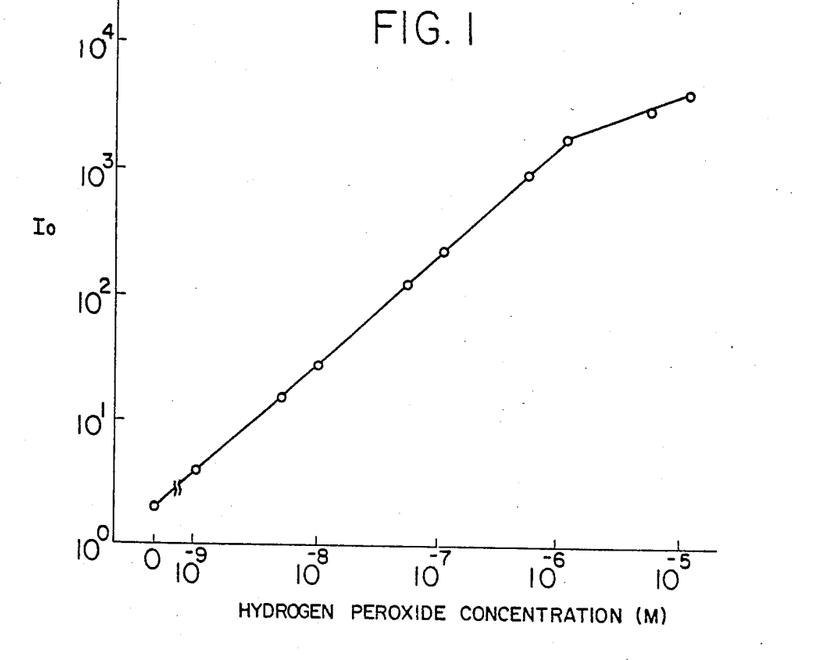
FIG. 1 is a graph illustrating the relation between the concentration (M) of hydrogen peroxide and the light emission intensity (relative value), Io, in the method for determination of hydrogen peroxide of the present invention.

As is seen from FIG. 1, hydrogen peroxide in a concentration of $10^{-9}M$ to $10^{-5}M$ can be determined.

REFERENCE EXAMPLE 1

To a mixed solvent [ethyl acetate/borate buffer solution/acetonitrile (1:1:8, v/v)] were added 2 mM hydrogen peroxide, 40 mM borate buffer solution (pH 10.5), 0.5 mM TCPO and 0.005% 8-anilinonaphthalene sulfonic acid, and serum in different concentrations. After 3 seconds, the light emission intensity was measured. The results are shown in FIG. 2 wherein the light emission intensities (ordinate, relative values) are plotted against the concentrations of serum (abscissae, dilution).

Figure 2:
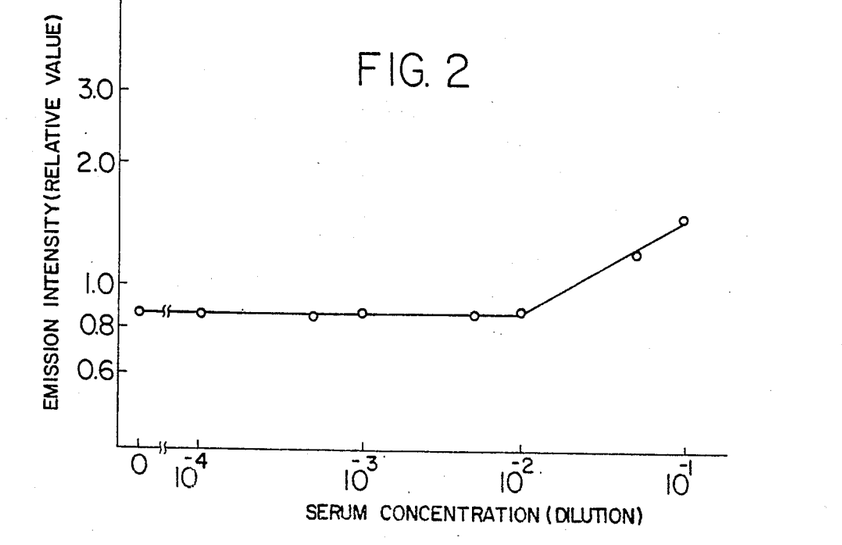
FIG. 2 is a graph illustrating the relation between the concentration (dilution) of serum and the light emission intensity (relative value) in the reaction of the fluorescent substance with the oxalic acid di-ester and hydrogen peroxide.

As is seen from FIG. 2, in the reaction of hydrogen peroxide with the oxalic acid di-ester (TCPO) and the fluorescent substance (8-anilinonaphtalene sulfonic acid), the light emission intensity is not affected by the serum in a concentration of 1/100 volume or lower. This concentration of serum (1/100 volume) is a suitable sample volume to use for ordinary clinical diagnosis. This shows that the method of the present invention wherein light emission from the reaction of hydrogen peroxide with the oxalic acid di-ester and the fluorescent substance is preferred as a chemiluminescence analysis for the determination of hydrogen peroxide derived from a component in serum.

EXAMPLE 2

A dispersion of 10 mM p-cresol in deionized water (0.4 ml) was placed in a vial and 25 mM phosphate buffer solution (2.6 ml, pH 7.0) was added to the vial. To the vial were added a solution of peroxidase in the above phosphate buffer solution (1 ml, 5 units/ml) and a sample solution containing a serial concentration of hydrogen peroxide and the mixture was incubated at 30° C. for 1 hour. Then, a solution of 0.1 mM TCPO and 0.4 mM hydrogen peroxide in acetonitrile (0.5 ml) was added to the resulting emitting solution (0.5 ml) with a syringe and a peak light emission was counted at 25° C. Light emission activity thus obtained was plotted against the concentrations of hydrogen peroxide. As the result, a linear relationship was obtained within a range of a concentration of $5 \times 10^{-7}$M to $10^{-4}$M. This reaction is based on an light emission reaction of the fluorescent substance resulting from oxidation polymerization with p-cresol at the time of addition of TCPO and hydrogen peroxide in acetonitrile.

EXAMPLE 3

A dispersion of 1.5 mM leucorhodamin B in 25 mM phosphate buffer solution (3 ml) was placed in a vial and a solution of peroxidase (1 ml, 5 units/ml) was added to the vial. A sample solution containing a serial concentration of hydrogen peroxide (1 ml) was added to the vial and the mixture was incubated at 30° C. for 1 hour. Then, a solution of 0.1 mM TCPO and 0.4 mM hydrogen peroxide in acetonitrile (0.5 ml) was added to the resulting emitting solution (0.5 ml) and a peak emission was counted at 25° C. A linear relationship between the light emission activity and the concentration of hydrogen peroxide was obtained within a range of $5 \times 10^{-8}$ to $10^{-4}$. This reaction is based on an emission reaction resulting from formation of the fluorescent substance by oxidation polymerization with leucorhodamin B and reaction thereof with TCPO and hydrogen peroxide.

EXAMPLE 4

Determination of Uric Acid

Preparation of non-fluorescent substance reagent:

Leucodiacetyl-2',7'-dichlorofluorescein (5 mg) was dissolved in ethanol (10 ml) and 0.01N sodium hydroxide (40 ml) was added thereto to hydrolyze acetyl group. To the mixture was added 25 mM phosphate butter solution (75 ml, pH 7.0) containing 2% β-cyclodextrin and the resulting mixture was stirred. An additional 25 mM phosphate buffer solution (pH 7.0) was added to adjust the total volume to 200 ml. This non-fluorescent substance reagent is stable for 2 days at room temperature.

Preparation of enzyme reagent:

Horseradish peroxidase and uricase were added to 25 mM phosphate buffer solution (pH 7.0) so that the concentration of peroxidase was 5 units/ml in terms of purpurogallin units and that of uricase was 1.5 units/ml.

Preparation of oxalic acid di-ester reagent:

0.5 mM Solution of TCPO in ethyl acetate and 2 mM solution of hydrogen peroxide in water were mixed and the volume of the mixture was adjusted with acetonitrile. The mixture was diluted 5 times with acetonitrile, when it was used.

Preparation of uric acid sample:

Uric acid was dispersed in 25 mM phosphate buffer solution in a concentration of $5 \times 10^{-6}$ mg/ml to $5 \times 10^{-2}$ mg/ml. As a control, 25 mM phosphate buffer solution containing no uric acid was used.

Figure 3:
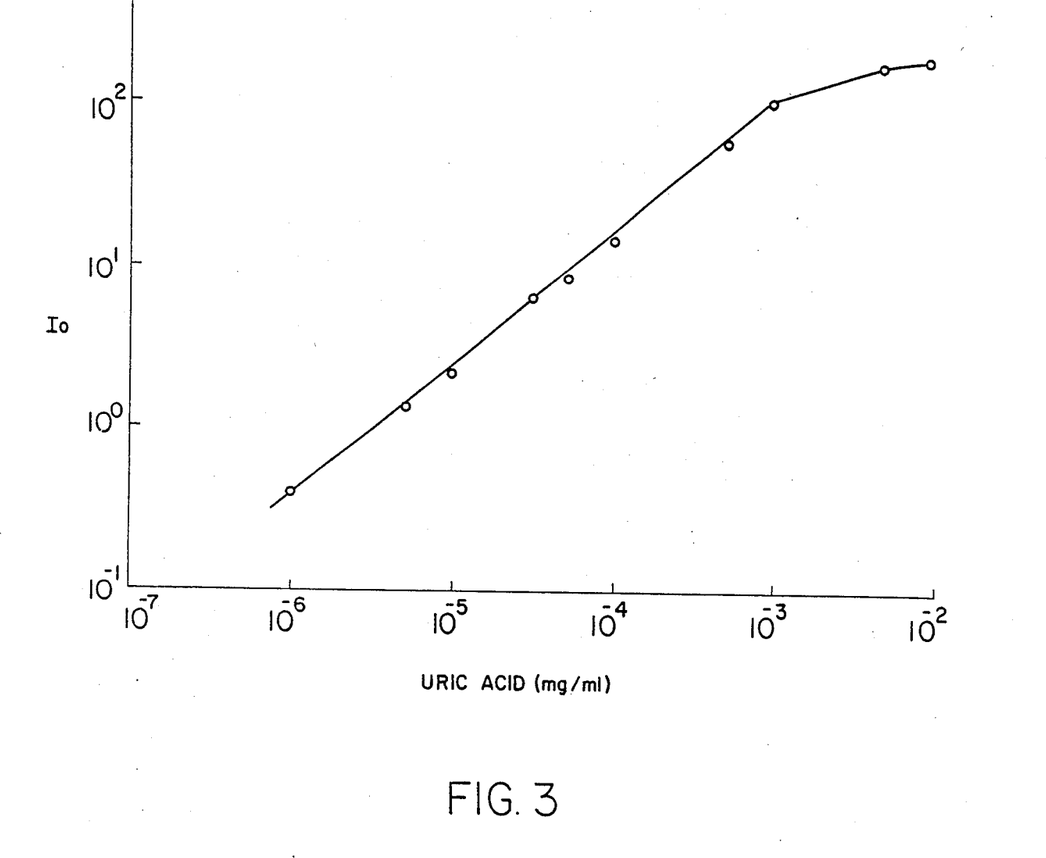
FIG. 3 is a graph illustrating the relation between the concentration of uric acid and the emission intensity (relative value), Io, in the method for determination of uric acid of the present invention.

Measurement:

The enzyme reagent (1 ml) and the uric acid sample (1 ml) were added to the non-fluorescent substance reagent (3 ml) and the mixture was incubated at 30° C. for 1 hour. The oxalic acid di-ester reagent (0.5 ml) was added to the resulting emitting mixture (0.5 ml) with a syringe and a peak emission was read. The results are shown in FIG. 3. The sensitivity was $10^{-6}$ mg/ml ($5.95 \times 10^{-9}$M) in the first reaction and a linear relationship was obtained within a range of a concentration of $10^{-6}$ mg/ml to $10^{-3}$ mg/ml.

Figure 4:
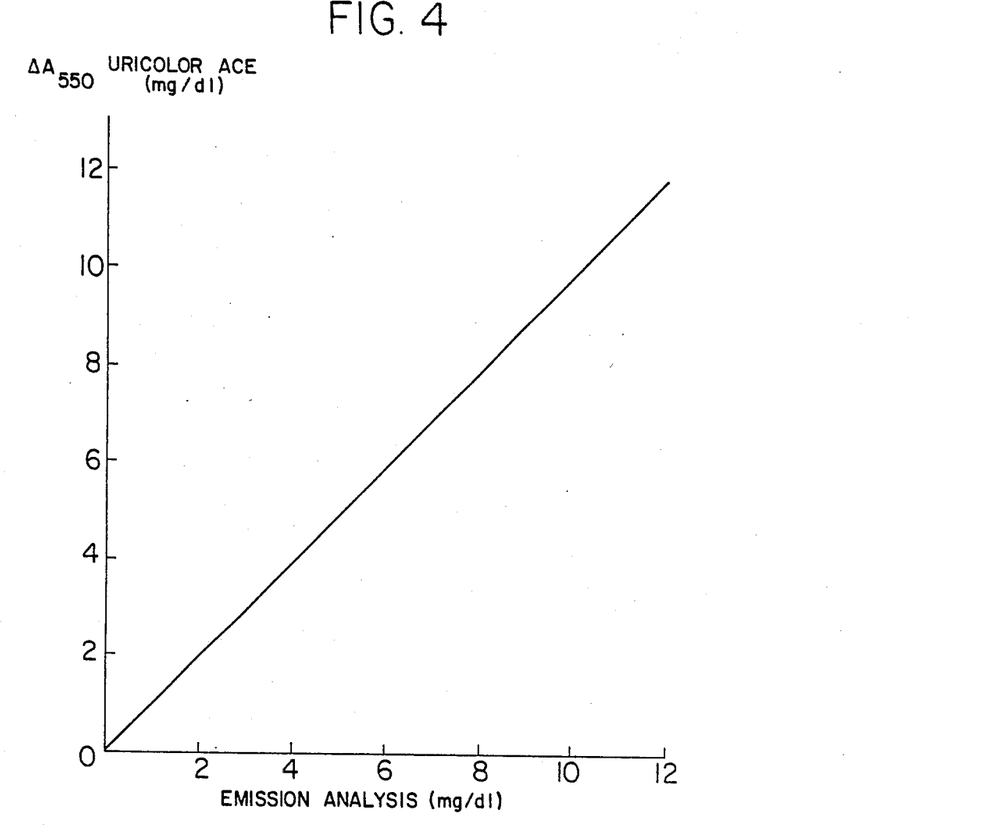
FIG. 4 is a graph illustrating the correlation between the method of the present invention and a conventional method wherein serum uric acid is determined in terms of an absorbency, A.

The same procedure was repeated except that a diluted serum (1/100, 1 ml) was used instead of the uric acid sample. The results were compared with those obtained by uric acid determination of the same diluted serum by a conventional absorption method using a commercially available uric acid determination reagent, Uricolor Ace (manufactured by Toyo Boseki Kabushiki Kaisha, Japan). As is seen from FIG. 4, both results are well correlated (y=0.987x+0.098, r=0.9991).

EXAMPLE 5

Determination of AFP

Preparation of anti-AFP bound solid phase:

Polystyrene balls (diameter 6.4 mm, 100 balls) were dipped in a solution of anti-AFP antibody in 0.1M sodium bicarbonate (20 ml) and the mixture was allowed to stand at 4° C. overnight. The balls were washed with physiological saline solution to obtain anti-AFP bonded polystyrene balls.

Preparation of glucose oxidase labelled anti-AFP:

Pepsin (1 mg) was added to anti-AFP antibody (20 mg) to hydrolyze at 37° C. overnight. The mixture was subjected to gel filtration using Sephadex G-150 to obtain F(ab')$_2$ fragment of anti-AFP antibody. To F(ab')$_2$ fragment thus obtained was added 0.1M 2-mercaptoethylamine (0.2 ml) and the mixture was reacted at 37° C. for 90 minutes. The reaction mixture was subjected to gel filtration using Sephadex G-25 to obtain Fab' fragment of anti-AFP antibody (7.3 mg). Separately, N-hydroxysuccinimidyl-N-(4-carboxycyclohexylmethyl)maleimide (1 mg) dissolved in dioxane was added in 3 to 4 portions to glucose oxidase (manufactured by Toyo Boseki Kabushiki Kaisha) (5 mg) and the mixture was subjected to gel filtration using Sephadex G-25 to obtain maleimidated glucose oxidase. Maleimidated glucose oxidase thus obtained and the above Fab' fragment of anti-AFP antibody (5 mg) were reacted at 4° C. overnight and then the mixture was subjected to gel filtration using Sephadex G-150. Active fractions were collected to obtain a glucode oxidase labelled anti-AFP.

Preparation of oxalic acid di-ester reagent:

Reagent (A) ... Fluorescin (5 mg) was dissolved in 25 mM phosphate buffer solution (200 ml).

Reagent (B) ... The reagent was prepared by mixing 100 mM hydrogen peroxide (600 μl), 5 mM TCPO solution (3 ml) and acetonitrile (26 ml). This reagent was diluted 5 times with acetonitrile when it was used.

These reagents A and B were prepared just prior to use them.

Measurement of AFP:

One anti-AFP bound polystyrene ball, a sample containing an unknown amount of AFP (50 μl) and 0.01M phosphate buffer solution (200 μl) were placed in a polystyrene tube (12×75 mm) and the mixture was reacted at 37° C. for 1 hour. The reaction mixture was washed with physiological saline solution. The glucose oxidase labelled anti-AFP was diluted 500 times with phosphate buffer solution containing 0.5% bovine serum albumin and the diluted glucose oxidase labelled anti-AFP (250 μl) was added to the above washed mixture and reacted at 37° C. for 1 hour. The mixture was again washed with physiological saline solution. Then, to the mixture was added 2% solution of glucose in 0.1M acetate buffer solution (250 μl) and reacted at 37° C. for 2 hours.

Then, the reaction mixture (100 μl) was placed in a test tube. The peroxidase solution (5 units/ml, 100 μl) and the reagent A (200 μl) were added to the tube and the mixture was reacted at 25° C. for 1 hour. The reaction mixture (300 μl) was placed in a vial for determination by LUMIPHOTOMETER TD4000 (manufactured by LABOSCIENCE CO., LTD.), the reagent B (500 82 l) was added thereto and the amount of emission was determined.

Figure 5:
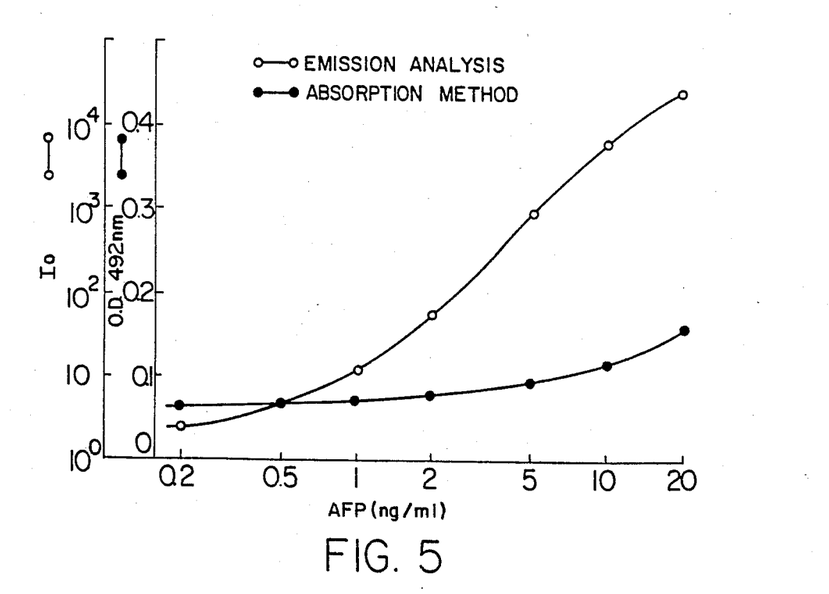
FIG. 5 is a graph illustrating calibration curves used for α-fetoprotein (hereinafter referred to as AFP) determination by the enzyme immunoassay of the present invention and for the reference example hereinafter.

Separately, the same procedure was repeated by using standard solutions containing known amounts of AFP to prepare a calibration curve as shown in FIG. 5.

The amount of AFP in the sample was calibrated based on the calibration curve.

As a reference example, AFP was determined by using "IMUNOBALL.AFP" (registered trade mark of solid phase for determination of AFP manufactured by Toyo Boseki Kabushiki Kaisha) according to the direction attached thereto. The results are also shown in FIG. 5.

As is seen from FIG. 5, AFP in a concentration of 0.2 to 0.5 ng/ml can be determined by the enzyme immunoassay of the present invention and the immunoassay shows remarkably higher sensitivity in comparison with the reference example.

EXAMPLE 6

Determination of CEA

Preparation of anti-CEA bound solid phase:

According to the same procedure for preparation of anti-AFP bound solid phase in Example 5, an anti-CEA bound solid phase was prepared by using anti-CEA antibody instead of anti-AFP antibody.

Preparation of peroxidase labelled anti-CEA:

Pepsin (1 mg) was added to anti-CEA antibody (20 mg) to hydrolyze at 37° C. overnight and the mixture was subjected to gel filtration using Sephadex G-150 to obtain F(ab')$_2$ fragment of anti-CEA antibody. To F(ab')$_2$ fragment thus obtained was added 0.1M 2-mercaptoethylamine (0.2 ml) and the mixture was reacted at 37° C. for 90 minutes. The mixture was subjected to gel filtration using Sephadex G-25 to obtain Fab' fragment of anti-CEA antibody (6.8 mg). Separately, N-hydroxysuccinimidyl-N-(4-carobxycyclohexylmethyl)maleimide (1.6 mg) dissolved in N,N'-dimethylformamide was added to peroxidase (manufactured by Toyo Boseki Kabushiki Kaisha) and the mixture was reacted at 30° C. for 60 minutes. The maleimide-peroxidase thus obtained and the above Fab' fragment of ahti-CEA antibody (2 mg) were reacted at 4° C. overnight and the reaction mixture was subjected to gel filtration using Ultrogel AcA 44. The active fractions were collected to obtain the peroxidase labelled anti-CEA.

Preparation of oxalic acid di-ester reagent:

According to the same procedure in Example 5, the reagents A and B were prepared.

Measurement of CEA:

One anti-CEA bound polystyrene ball, a sample containing an unknown amount of CEA (50 μl) and 0.01M phosphate buffer solution (200 μl) were placed in a polystyrene tube (12×75 mm) and the mixture was reacted at 37° C. for 1 hour. The reaction mixture was washed with physiological saline solution. To the mixture was added the peroxidase labelled anti-CEA diluted 750 times with phosphate buffer solution containing 0.5% bovine serum albumin (250 μl) and the mixture was reacted at 37° C. for 1 hour. The reaction mixture was washed with physiological saline solution.

Then, 5 mM solution of hydrogen peroxide (100 μl) and the reagent A (300 μl) were added and the mixture was reacted at 25° C. for 1 hour. The reaction mixture (300 μl) was placed in a vial for determination by LUMIPHOTOMETER TD 4000 (manufactured by LABOSCINECE CO., LTD.). The reagent B (500 μl) was added and the amount of emission was determined.

Separately, according to the same procedure, measurement were repeated by using standard solutions containing known amounts of CEA to prepare a calibration curve.

The amount of CEA in the sample was calibrated based on the calibration curve. According to this method, 0.1 ng/ml of CEA can be determined. This sensitivity is remarkably higher than that of a conventional absorption method.

EXAMPLE 7

Evaluation of bactericidal activity of leukocytes

Collection of leukocytes (neutrophils):

Venous blood of a normal healthy person was collected with heparin (5 IU/ml) and neutrophils were separated from the blood by using Dextran, Percoll-Hypaque. Neutrophils were suspended in phosphate buffered saline containing $CaCl_2$ (0.9 mM), $MgCl_2$ (0.5 mM) and glucose (1 g/l) (PBS/Ca/Mg/glucose). As a stimulant for neutrophils, zymosan opsonized with human fresh serum was used by adjusting the concentration to 5 mg/ml.

Preparation of $H_2O_2$ calibration curve:

A hydrogen peroxide calibration curve was prepared by using various standard solutions of different amounts of hydrogen peroxide in PBS/Ca/Mg/glucose (1 ml each) as follows:

Leucodiacetyl-2',7'-dichlorofluorescein (5 mg) was dissolved in ethanol (10 ml) and 0.01N sodium hydroxide (40 ml) was added to the solution to effect deacetylation to obtain activated leucodichlorofluorescein. To the reaction mixture was added 25 mM phosphate buffer solution (pH 7.0, 75 ml) containing 2% β-cyclodextrin and the mixture was stirred to prepare the non-fluorescent substance reagent.

Separately, 0.5 mM bis-(2,4,6-trichlorophenyl)oxalate and 2 mM hydrogen peroxide were mixed and the mixture was diluted 5 times with acetonitrile to prepare the oxalic acid di-ester reagent.

Peroxiderse was dissolved in 25 mM phosphate buffer solution (pH 7.0) in the concentration of 5 U/ml to prepare the peroxidase solution.

Each standard solution of hydrogen peroxide (1 ml) was added to a mixture of the above non-fluorescent substance reagent (3 ml) and the peroxidase solution (1 ml) and the mixture was allowed to stand at 30° C. for 1 hour. To the reaction mixture (0.5 ml) was added the oxalic acid di-ester reagent (0.5 ml) and the peak value of light emission was determined by using LUMIPHO-TOMETER TD 4000. As the result, a linear relationship between concentrations of hydrogen peroxide in the standard solutions and the peak values was obtained within the range of $10^{-9}M$ to $10^{-5}M$ of hydrogen peroxide.

Measurement of $H_2O_2$ releasing ability of neutrophils:

Effect of zymosan on the ability of releasing hydrogen peroxide of neutrophils was determined by adding the above opsonized zymosan containing 1 μg to 500 μg of zymosan to the neutrophil suspension (1 ml, $2 \times 10^5$ cells).

Figure 6:
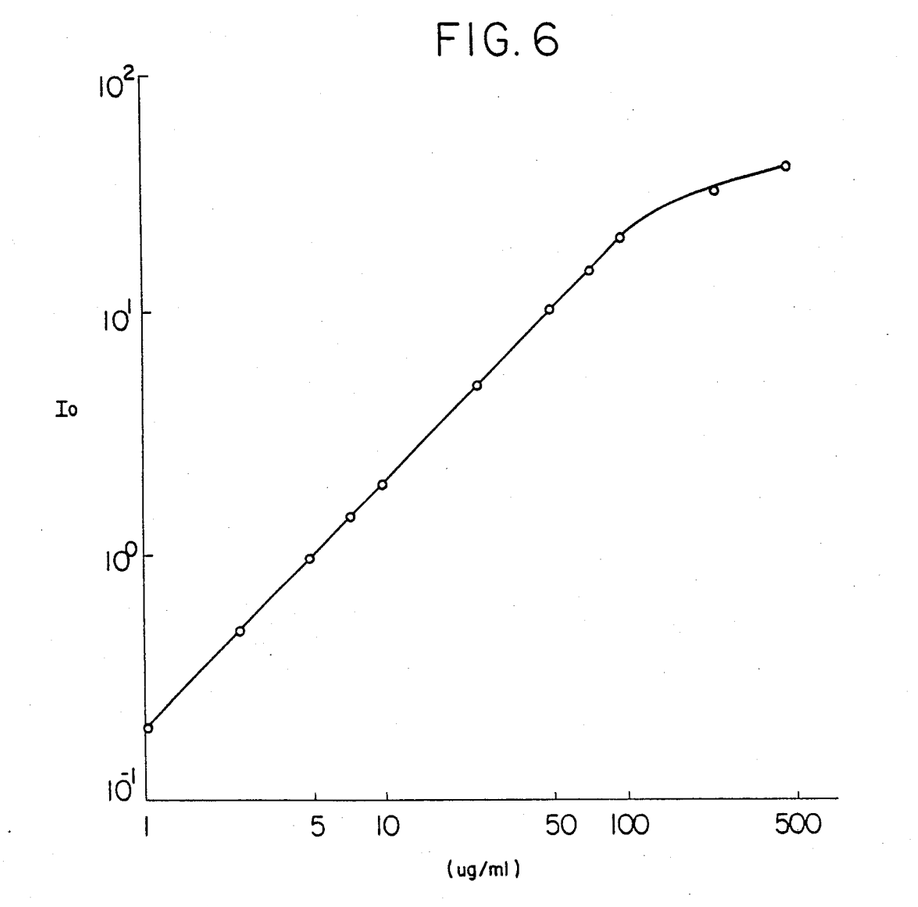
FIG. 6 is a graph illustrating the relation between the concentration of zymosan in μg/ml on the x-axis and the light emission intensity (relative value), Io, on the y-axis in the method for evaluation of bactericidal activity in phagocytosis of leukocytes of the present invention.

After addition of the zymosan solution (1 ml) to the neutrophil suspension, the mixture was reacted at 37° C. for 1 hour and then the reaction was halted by addition of EDTA-glycine buffer (1 ml). The reaction mixture was centrifuged at $2,000 \times g$ for 10 minutes. The supernatant was neutralized, a sample of the neutralized supernatant (1 ml) was mixed with the above non-fluorescent substance regent (3 ml) and the peroxidase solution (1 ml, 5 U/ml) and the mixture was reacted at 30° C. for 1 hour. The reaction mixture (0.5 ml) was mixed with the above oxalic acid di-ester reagent (0.5 ml) and the peak value of emission was determined. The blank value was subtracted from the peak value determined. As the result, a linear relationship was obtained within the range of 1 g to 100 g of zymosan as shown in FIG. 6 wherein the emission intensity (relative value, ordinate), Io, was plotted against the concentration of zymosan added (abscissa). This result shows that the sensitivity of this method is increased one order of the concentration of zymosan over that of a conventional method.

What is claimed is:

1. A method for determination of hydrogen peroxide by chemiluminescence analysis which comprises the steps of
   (a) reacting a sample containing hydrogen peroxide with an oxidizable non-fluorescent substance in the presence of an oxidizing catalyst in an aqueous reaction system to convert the non-fluorescent substance to a fluorescent substance,
   (b) reacting the fluorescent substance with an oxalic acid di-ester and hydrogen peroxide in the presence of an inhibitor for the oxidizing catalyst whereby the oxidizing catalyst is inactivated, and then
   (c) measuring the amount of light emitted from reaction (b) to determine the amount of hydrogen peroxide contained in the sample.

2. A method according to claim 1, wherein the oxidizable non-fluorescent substance is a member selected from the group consisting of leucofluorescein, 2′,7′-dichlorofluoresceine-diacetate, leucorhodamin, leucoeosin, homovanillic acid, p-cresol, 3-(p-hydroxyphenyl)propionic acid and thyramine and is present in an amount of 0.001 to 5 mM in the aqueous reaction system.

3. A method according to claim 1, wherein the oxidizing catalyst is a member selected from the group consisting of peroxidase, microperoxidase, myeloperoxidase, hemin, hematine, catalase and potassium ferricyanide.

4. A method according to claim 1, wherein the oxalic acid di-ester is a member selected from the group consisting of bis(2,4,6-trichlorophenyl)oxalate and bis(2,4-dinitrophenyl)oxalate and is present in an amount of 0.1 to 50 mM in the reaction thereof with the fluorescent substance.

5. A method according to claim 1, wherein hydrogen peroxide is present in an amount of 0.1 to 50 mM in the reaction thereof with the fluorescent substance.

6. A method according to claim 1, wherein the reaction of hydrogen peroxide in the sample with the non-fluorescent substance is performed at a temperature of about 20° to 30° C. at pH 5 to 9.

7. A method according to claim 1, wherein a cyclodextrin is added to the aqueous reaction system in an amount of $10^{-5}$ to $10^{-1}M$.

8. A method according to claim 1, wherein zinc sulfate hepta hydrate is added to the aqueous reaction system to produce a final concentration of zinc sulfate hepta hydrate of about 0.04 mg/ml.

9. A method according to claim 1, wherein the reaction of the fluorescent substance with the oxalic acid di-ester and hydrogen peroxide is performed at a temperature of about 20° to 40° C. at pH of 8 to 12.

10. A method according to claim 1, wherein the reaction of the fluorescent substance with the oxalic acid di-ester and hydrogen peroxide is performed in an organic solvent containing water wherein the organic solvent is the inhibitor for the oxidizing catalyst.

11. A method according to claim 10, wherein the organic solvent is a member selected from the group consisting of ethyl acetate, acetone, acetonitrile and a mixture thereof.

12. A method according to claim 1, wherein the inhibitor is a member selected from the group consisting of potassium cyanide, sodium cyanide, sodium azide, sulfides, fluorides, hydroxyphenylhydrazine, 2,3-dimercaptopropanol and organic solvent.

13. A method according to claim 12, wherein the organic solvent is a member selected from the group consisting of ethyl acetate, acetonitrile, ethanol and acetone.

14. A method according to claim 1, wherein hydrogen peroxide in the sample is derived from a component of a body fluid.

15. A method according to claim 14, wherein the body fluid is blood, urine, saliva or tears.

16. A method according to claim 1, wherein the sample is obtained from a reaction mixture of enzyme immunoassay, and hydrogen peroxide in the sample is derived from a physiologically active substance to be determined by the enzyme immunoassay in an immunological reaction for quantitative production of hydrogen peroxide from the physiologically active substance.

17. A method according to claim 16, wherein the physiologically active substance is selected from the group consisting of peptide hormones, steroid hormones, fetal proteins, immunoglobulins, antiviral antibodies developed in various infections and autoantibodies developed in collagen disease.

18. A method according to claim 16, wherein the enzyme immunoassay is performed by subjecting the physiologically active substance in a body fluid sample to an immunological reaction by using an enzyme which is capable of formation of hydrogen peroxide as a labelling enzyme, adding a substrate for the enzyme to form hydrogen peroxide, reacting hydrogen peroxide thus formed with the oxidizable non-fluorescent substance in the presence of the oxidizing catalyst to convert the non-fluorescent substance into the fluorescent substance, reacting the fluorescent substance with the oxalic acid di-ester and hydrogen peroxide in the presence of an inhibitor for the oxidizing catalyst whereby the oxidizing catalyst is inactivated and then determining the amount of light emitted from the reacting of the fluorescent substance with the oxalic acid di-ester and hydrogen peroxide.

19. A method according to claim 18, wherein the oxidizing catalyst is peroxidase.

20. A method according to claim 18, wherein the enzyme which is capable of formation of hydrogen peroxide is a member selected from the group consisting of glucose oxidase, cholesterol oxidase, choline oxidase and an amino acid oxidase.

21. A method according to claim 20, wherein the enzyme is glucose oxidase.

22. A method according to claim 1, wherein the sample is a suspension of leukocytes showing phagocytosis.

23. A method for determination of a component of a body fluid by chemiluminescence analysis which comprises the steps of
  (a) reacting a component in a sample from a body fluid or a substance formed by an enzymatic reaction of an enzyme in a sample from a body fluid with an oxidase to form hydrogen peroxide,
  (b) reacting the hydrogen peroxide thus formed with an oxidizable non-fluorescent substance in the presence of an oxidizing catalyst in an aqueous reaction system to convert the non-fluorescent substance to a fluorescent substance,
  (c) reacting the fluorescent substance with an oxalic acid di-ester and hydrogen peroxide in the presence of an inhibitor for the oxidizing catalyst whereby the oxidizing catalyst is inactivated, and then
  (d) measuring the amount of light emitted from reaction (c) to determine the amount of the component of the enzymatic activity in the sample from the body fluid.

24. A method according to claim 23, wherein the sample from the body fluid is blood, urine, saliva or tears.

25. A method according to claim 23, wherein the component of the body fluid is selected from the group consisting of uric acid, cholesterols, glucose, creatinine, polyamines, triglycerides, lactates, pyruvates and fatty acids.

26. A method according to claim 23, wherein the inhibitor is a member selected from the group consisting of potassium cyanide, sodium cyanide, sodium azide, sulfides, fluorides, hydroxyphenylhydrazine, 2,3-dimercaptopropanol and organic solvents.

27. A method according to claim 23, wherein the organic solvent is a member selected from the group consisting of ethyl acetate, acetonitrile, ethanol and acetone.

28. A method for determination of a physiologically active substance which comprises the steps of
  (a) performing enzyme immunoassay of the physiologically active substance in a reaction mixture using peroxidase as a labeling enzyme,
  (b) obtaining a sample of the reaction mixture of the enzyme immunoassay,
  (c) reacting the sample with hydrogen peroxide and oxidizable non-fluorescent substance in an aqueous reaction system to convert the non-fluorescent substance to a fluorescent substance,
  (d) reacting the fluorescent substance with an oxalic acid di-ester and hydrogen peroxide in the presence of an inhibitor for peroxidase whereby the peroxidase is inactivated, and then
  (e) measuring the amount of light emitted from reaction (d) to determine the amount of the physiologically active substance.

29. A method according to claim 28, wherein the physiologically active substance is selected from the group consisting of peptide hormones, steroid hormones, fetal proteins, immunoglobulins, antiviral antibodies developed in various infections and autoantibodies developed in collagen disease.

30. A method according to claim 28, wherein the inhibitor is a member selected from the group consisting of potassium cyanide, sodium cyanide, sodium azide, sulfides, fluorides, hydroxyphenylhydrazine, 2,3-dimercaptopropanol and organic solvent.

31. A method according to claim 30, wherein the organic solvent is a member selected from the group consisting of ethyl acetate, acetonitrile, ethanol and acetone.

* * * * *